United States Patent
Grodzki

(10) Patent No.: US 9,395,429 B2
(45) Date of Patent: Jul. 19, 2016

(54) METHOD AND MAGNETIC RESONANCE DEVICE FOR IMAGE ACQUISITION

(71) Applicant: David Grodzki, Erlangen (DE)

(72) Inventor: David Grodzki, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 437 days.

(21) Appl. No.: 14/050,613

(22) Filed: Oct. 10, 2013

(65) Prior Publication Data

US 2014/0103928 A1 Apr. 17, 2014

(30) Foreign Application Priority Data

Oct. 10, 2012 (DE) .......................... 10 2012 218 422

(51) Int. Cl.
| | | |
|---|---|---|
| *G01V 3/00* | (2006.01) | |
| *G01R 33/48* | (2006.01) | |
| *G01R 33/56* | (2006.01) | |
| *A61B 5/055* | (2006.01) | |

(52) U.S. Cl.
CPC ........ *G01R 33/4828* (2013.01); *G01R 33/4816* (2013.01); *G01R 33/5602* (2013.01); *A61B 5/055* (2013.01); *G01R 33/4824* (2013.01)

(58) Field of Classification Search
USPC ........................................................ 324/309
See application file for complete search history.

(56) References Cited

U.S. PATENT DOCUMENTS

| | | | | |
|---|---|---|---|---|
| 2001/0033162 | A1* | 10/2001 | Harvey | G01R 33/561 324/307 |
| 2002/0135366 | A1 | 9/2002 | Heubes | |
| 2005/0073303 | A1* | 4/2005 | Harer | G01R 33/4824 324/307 |
| 2005/0261576 | A1 | 11/2005 | Speier et al. | |
| 2010/0117644 | A1 | 5/2010 | Nimbargi et al. | |
| 2011/0215804 | A1* | 9/2011 | Deimling | G01R 33/4816 324/307 |
| 2011/0288398 | A1* | 11/2011 | Park | G01R 33/4816 600/410 |
| 2012/0074938 | A1 | 3/2012 | Grodzki et al. | |

OTHER PUBLICATIONS

Heid et al. "Rapid Single Point (RASP) Imaging", SMR, 3rd Annual Meeting, p. 684, (1995).
Nielles-Vallespin et al., "3D Radial Projection Technique with Ultrashort Echo Times for Sodium MRI: Clinical Applications in Human Brain and Skeletal Muscle", in: Magnetic Resonance in Medicine, vol. 57, (2007), pp. 74-81.
Grodzki et. al.; "Ultrashort echo time imaging using pointwise encoding time reduction with radial acquisition (PETRA)"; in: Magn. Reson. Med.; vol. 67; (2011); pp. 510-518.
Chamerlain et al: "Quiet T1- and T2-weighted brain imaging using SWIFT", Proc. Intl. Soc. Mag. Reson. Med. 19, (2011), p. 2723.
Brant-Zawadzki et al: "MP RAGE: a three-dimensional T1-weighted, gradient-echo sequence-initial experience in the brain", Radiology vol. 182, pp. 769-775, (1992).

* cited by examiner

*Primary Examiner* — Rodney Fuller
(74) *Attorney, Agent, or Firm* — Schiff Hardin LLP

(57) ABSTRACT

In a method and magnetic resonance apparatus for acquiring image data using a sequence in which k-space corresponding to the imaging area is scanned in a first region of k-space, which does not include the center of k-space, radially along spokes emanating from the center of k-space, with at least two phase coding gradients being completely ramped up before the excitation pulse, and in a second central region of k-space, which remains without the first region, in a Cartesian manner. For contrast increase, a pre-pulse is provided before a predetermined number of individual measurements. A portion of the measurement points of the second region of k-space, which portion is situated nearest the center of k-space, is scanned as central measurement points after the first administration of the pre-pulse immediately following a zero crossing of the contrast-relevant magnetization of one of at least two materials in the image.

11 Claims, 3 Drawing Sheets

METHOD AND MAGNETIC RESONANCE DEVICE FOR IMAGE ACQUISITION

BACKGROUND OF THE INVENTION

1. Field of the Invention

The invention concerns a method for image acquisition with a magnetic resonance device using a magnetic resonance sequence (in particular a PETRA sequence), of the type in which k-space corresponding to the imaging area is scanned, with a first region of k-space that does not include the center of k-space being scanned radially along a number of spokes emanating from the center of k-space, and wherein at least two phase coding gradients are already ramped up completely before radiation of the excitation pulse, and a second central region of k-space that remains without the first region is scanned in a Cartesian manner (in particular by single point imaging), and wherein, for the purpose of a contrast increase, a pre-pulse (in particular an inversion pulse to establish a T1 contrast) is provided before a determined number of individual measurements. The invention also concerns a magnetic resonance device for implementing such a method.

2. Description of the Prior Art

Data acquisition sequences with ultrashort echo times (thus echo times TE<0.5 ms) offer new fields of application in magnetic resonance imaging. They enable the depiction of substances that are not visible with conventional magnetic resonance sequences (for example spin echo or gradient echo sequences) since their repetition time T2 is markedly shorter than the echo time and their signal has already decayed at the acquisition point in time. Some magnetic resonance sequences with ultrashort echo times are also extremely quiet since only extremely small gradient changes are necessary. Examples of such sequences that markedly reduce exposure of the patient to noise are the zTE (zero TE sequence), the WASPI sequence (Water and Fat Suppressed Proton Projection MRI), the SWIFT sequence (Sweep Imaging with Fourier Transformation) and the PETRA sequence (Pointwise Encoding Time reduction with Radial Acquisition).

A number of magnetic resonance sequences with ultrashort echo time have already been proposed, for example the radial UTE sequence ("Ultrashort Echo Time", see for example the article by Sonia Nielles-Vallespin, "3D radial projection technique with ultrashort echo times for sodium MRI: clinical applications in human brain and skeletal muscle", Magn. Reson. Med. 2007; 57; Pages 74-81). After a wait time after an excitation pulse, the gradients are ramped up and begun simultaneously with the data acquisition. The k-space trajectory that is scanned in such a manner after an excitation travels radially outward from the center of k-space. Therefore, before the reconstruction of the image data (by means of Fourier transformation) starting from raw data acquired in k-space, the raw data are initially transformed onto a Cartesian k-space grid (for example via regridding).

A further approach in order to enable short echo times is to scan k-space in points by detecting the free induction decay (FID). Such a method is also designated as single point imaging, since essentially only one raw data point in k-space is detected for each radio-frequency pulse. An example of such a method for single point imaging is the RASP method ("Rapid Signal Point Imaging", O. Heid. et al, SMR, 3rd Annual Meeting, Page 684, 1995). A raw data point in k-space is read out at the echo time TE at a fixed point in time after the radio-frequency excitation pulse. The phase of this raw data point is coded by gradients that are changed by the magnetic resonance device for each raw data point or measurement point, so that k-space can be scanned point by point.

A further shortening of the echo time and of the total acquisition time is enabled by the PETRA sequence, which is described by DE 10 2010 041 446 A1 and an article by D. Grodzki et al., "Ultrashort Echo Time Imaging Using Pointwise Encoding Time Reduction With Radial Acquisition (PETRA)", Magnetic Resonance in Medicine 67, Pages 510-518, 2012. These publications are incorporated herein by reference. In the PETRA sequence, k-space corresponding to the imaging area is read out in two different ways. A first region which does not include the center of k-space is scanned in that at least two phase coding gradients are initially switched in a respective spatial direction by means of a gradient system of a magnetic resonance device, wherein only after reaching the full strength of the switched phase coding gradients is a non-selective radio-frequency excitation pulse radiated by means of a radio-frequency transmission/reception device of the magnetic resonance device. After a time t1 after the last radiated excitation pulse, echo signals are acquired of the radio-frequency transmission/reception device (or an additional, possibly dedicated radio-frequency reception device) and these are stored as raw data points along the radial k-space trajectories (spokes) predetermined by the strength of the phase coding gradients. These steps are repeated until k-space corresponding to the imaging area is read out along radial k-space trajectories in the first region depending on time t1. The switching (activation) of the phase coding gradients and the wait until these are ramped up can be further reduced to the echo time, for example in comparison to the UTE sequence. However, a central, spherical region including the center of k-space—the aforementioned second region of k-space—cannot be scanned, because the phase coding gradients have already been ramped up. Consequently, this second region of k-space (which is not covered in the aforementioned first region of k-space and which includes the center of k-space) is scanned differently, with the scanning thereof taking place in a Cartesian manner, in particular by a single point imaging method (for example RASP). Since the raw data acquired in this second portion of the scanning are already situated on a Cartesian k-space grid, while the radially read-out raw data must still be transformed into such a grid (as explained above) before image data can be reconstructed from the raw data by means of Fourier transformation, an additional savings of cost and time results.

The contrast of magnetic resonance sequences with ultrashort echo time (in particular thus also the PETRA sequence) lies in the range of proton density weighting to T1 weighting. Given constant repetition time and constant flip angle over the measurement, what is known as a steady state develops that determines the precise contrast. In the zTE, WASPI, SWIFT and PETRA sequence, the flip angles are often limited to less than approximately eight to twelve degrees, which leads to a predominantly proton density-weighted contrast given typical repetition times of 3 to 5 ms.

In order to obtain a T1 or also a T2 contrast, it was proposed to use pre-pulses which are respectively applied before at least one part of the measurement processes. To save time, it is thus conceivable to apply the pre-pulses only every n repetitions, which (for example) is described in the article "Quiet T1- and T2-weighted brain imaging using SWIFT", Proc. ISMRM 2011, Page 2723 by R. Chamberlain et al.

For the MPRAGE sequence (see for example the article by M. Brant-Zawadzki et al., "MP RAGE: a three-dimensional T1-weighted, gradient-echo sequence—initial experience in the brain", Radiology 182, Pages 769-775, 1992), individual k-space lines are scanned in a Cartesian manner. If pre-pulses are also used here, after the pre-pulse a defined time $T_{VP}$ is initially waited here, whereupon an acquisition duration of $T_{ACQ}$ follows in which a number of $n=T_{ACQ/TR}$ repetitions are measured, wherein TR designates the repetition time (as is typical). After the acquisition duration, a wait time can further be provided before the next pre-pulse is applied. During the wait time, the spins relax, which can possibly be advantageous for the signal-to-noise ratio, wherein a complete relaxation typically no longer occurs, however.

This is explained using the example of an inversion pulse for the T1 weighting. The spins are initially inverted (i.e., rotated by a flip angle of 180°) by the pre-pulse formed as an inversion pulse. If excitation pulses that concern a smaller flip angle are now provided in the relaxation (always spaced by the repetition time), a stability magnetization that does not correspond to the maximum transversal magnetization results depending on the relaxation of the respective material, given which stability magnetization the relaxation time is ultimately "stopped" by the excitation pulses. This stability magnetization is different for different materials (for example grey and white brain matter). A T1 weighting results from this.

If the data acquisition is then interrupted for the new pre-pulses, a complete relaxation also does not occur, so that consequently a rotation out of the maximum transverse magnetization does not occur, but rather either a rotation directly out of the stability magnetization or by a value between the maximum transverse magnetization and the stability magnetization. A steady state therefore results after a specific time (a transient event), which means that the curves of the magnetizations are the same for each cycle of pre-pulse and measurement process.

In the MPRAGE sequence measurement takes place only in the steady state, which has engaged at the beginning of the complete measurement after a few of these cycles (in part already after one cycle). Often, a wait over a pair of these cycles is implemented, in order to not contaminate the measurement with data from the transient event.

A procedure is known to optimize the MPRAGE sequence so that an optimally good contrast—for example between grey and white brain matter—is achieved with an optimally high SNR. For this purpose, an optimized point in time TI after the administration of the pre-pulse is determined, in which an optimally good contrast is provided (for example a clear difference between the transverse magnetization components) but the absolute value (of the transverse magnetization components, for example) is large enough that the signal-to-noise ratio is sufficiently high. A balancing ultimately takes place, from the result of which an optimal point in time TI can be derived that typically is during the relaxation process, before reaching the stability magnetization discussed above.

For the MPRAGE it was now proposed that the k-space lines that are closest to the k-space center and those that are most decisive for the contrast and the signal-to-noise ratio are specifically measured at the optimized point in time T1 after the administration of the pre-pulse.

Due to the different principle, this procedure in the MPRAGE sequence cannot be directly transferred to the PETRA sequence.

SUMMARY OF THE INVENTION

An object of the present invention is to improve the contrast and the signal-to-noise ratio even in a magnetic resonance sequence (in particular the PETRA sequence) that combines a radial scanning of k-space and a Cartesian scanning of k-space.

This object is achieved in accordance with the invention by a method of the aforementioned type wherein, according to the invention, at least one portion of the measurement points of the second region of k-space that are closest to the center of k-space is scanned as a central measurement point after the first radiation of the pre-pulse following—preferably immediately following—a zero crossing of the magnetization (which serves for contrast) of one of the at least two materials to be differentiated in the image exposure.

In accordance with the invention, raw measurement data are entered at a defined number of k-space points around the center of k-space (for example $3^3$, $4^3$ or $5^3$ points) immediately after the very first pre-pulse (for example an inversion pulse). After the very first pre-pulse, the spin system still has not reached in the steady state (as discussed above) and the transverse magnetization achieves markedly greater values than in the steady state. A second advantage of such an early measurement of the points in the region of the center of k-space is that the first pre-pulse is radiated during a maximally relaxed magnetization, such that it is consequently possible to analytically determine (due to the clearly defined starting position) a point in time at which a contrast and/or signal-to-noise ratio that is optimal for the measurement is present. This is discussed in further detail in the following.

Because the center of k-space is decisive for the contrast and the signal-to-noise ratio of the image exposure, in this way the contrast can be stabilized and the signal-to-noise ratio can be increased.

For the T1 contrast, the essential point is that more transverse magnetization is present in the transient event, and a greater response can be realized in the magnetizations of the materials to be differentiated than in the steady state. Given T2 pre-pulses to generate T2 contrasts—for example a series of inversions, refocusings and the like—a completely relaxed magnetization (which is present at the first application of the pre-pulse) is appropriate for a good contrast, such that a very good contrast can be achieved while a sub-optimal contrast is present in the steady state. The measurement points (and radial spokes) situated further out in k-space are consequently measured in the steady state.

In the method according to the invention, exactly the opposite of what was done as presented above in the MPRAGE sequence is consequently implemented, because measurement does not always take place in the steady state; rather, the k-space center is specifically measured in the transient event leading to the steady state after the very first pre-pulse—the sequence of pre-pulse and following measurements (acquisition time period) is designated as a cycle, thus the very first cycle.

It is particularly advantageous for the measurement to start after the pre-pulse when the transversal magnetization of one of multiple (for example two) materials to be differentiated has its zero crossing. Other magnetizations are already further relaxed at this point in time, which means that in particular the zero crossing that chronologically takes place last is considered in particular. For example, if grey and white brain matter are to be differentiated as materials, for the transient event after the first application of an inversion pulse to generate a T1 contrast it applies that the transverse magnetization of the white brain matter is already relaxed to nearly 50%—consequently delivers a high signal contribution—while the grey brain matter has its zero crossing. In successive measurement cycles (comprising pre-pulse and acquisition time period), the steady state engages and the transversal magnetization of the white brain matter is markedly lower at the zero crossing of the transversal magnetization of the grey brain matter, such that no difference expressed in such a way is provided, and in particular lower transverse magnetizations are present, which has a negative effect on the signal-to-noise ratio.

It is noted that the present invention in general also enables the acquisition time periods in the remainder of the sequence to not be realized in an ideal compromise between contrast and signal-to-noise ratio, such that a measurement can also occur at points in time in which no expressed difference is achieved between the signals of different materials. This is due to the fact that the center of k-space, which is important to contrast, has already been scanned with optimal contrast.

Overall, the contrast-to-noise ratio—and primarily the signal-to-noise ratio—can thus be markedly increased, particularly in comparison to the case in which an optimal measurement point in time is determined that occurs during the steady state.

In a further embodiment of the present invention, the measurement (acquisition) of the data to be entered at the central k-space points is begun after a start time of T1 (of the one of the at least two materials to be differentiated in the image exposure) times In(2) after the administration of the pre-pulse. As already noted, the clearly defined starting position (in particular thus the complete relaxation of the transverse magnetization) enables an ideal point in time to be determined. In particular, the chronologically last zero crossing of one of the materials to be differentiated is selected, which results in a start time of TI=In(2)*T1. In the example of the differentiation of white and grey brain matter, the zero crossing of the transverse magnetization of the grey brain matter can be considered.

Initially, a central measurement point corresponding to the center of k-space can be measured. If the best contrast is provided at the zero crossing, it is recommended to measure the center of k-space at the next placed measurement point (in particular the measurement point placed in the center of k-space, which is predominantly responsible for the contrast) at this optimal point in time (for example calculated as just described) in order to then consider only additional points in the region of the k-space center.

As already noted, the $n^3$ points situated closest to the center of k-space can be measured as central measurement points with n=2, 3, 4 or 5. For example, the most central 27 or 125 measurement points can be measured as central measurement points.

In a further embodiment of the present invention, the central measurement points are measured along a spiral-like measurement trajectory in k-space, starting from the central measurement point situated closest to the center of k-space. It is thus conceivable to measure the central measurement points ultimately ordered according to their distance from the center of k-space in that a corresponding measurement trajectory (in particular a spiral-like measurement trajectory in k-space) is selected. It should be noted that such measurement trajectories (acquisition trajectories) are also implemented without large jumps with regard to the phase coding gradients, such that no noise development arises and the sequence overall remains quiet.

In general, the method according to the invention thus utilizes the fact that the center of k-space (included in the first region of k-space) is scanned anyway in a Cartesian manner, in particular by single point imaging, in order to "give preference" to a defined portion of the measurement points of the second region of k-space in their measurement, and to already conduct their measurement in the first region before the acquisition of the radial spokes. This is possible without forcing large jumps in the phase coding gradients, which could diminish the advantage that the magnetic resonance sequence can be implemented extremely quietly.

In addition to the method, the present invention also concerns a magnetic resonance device that has a control device designed to implement the method according to the invention. Magnetic resonance devices are known that have control devices that control the specific image acquisition, and consequently can also conduct the method according to the invention so as to cause the measurement to occur in an order in which measurement already takes place in the transient event leading to the steady state. All embodiments with regard to the method according to the invention apply analogously to the magnetic resonance device according to the invention, as well as the advantages achieved with the method.

DESCRIPTION OF THE PREFERRED EMBODIMENTS

Figure 1:
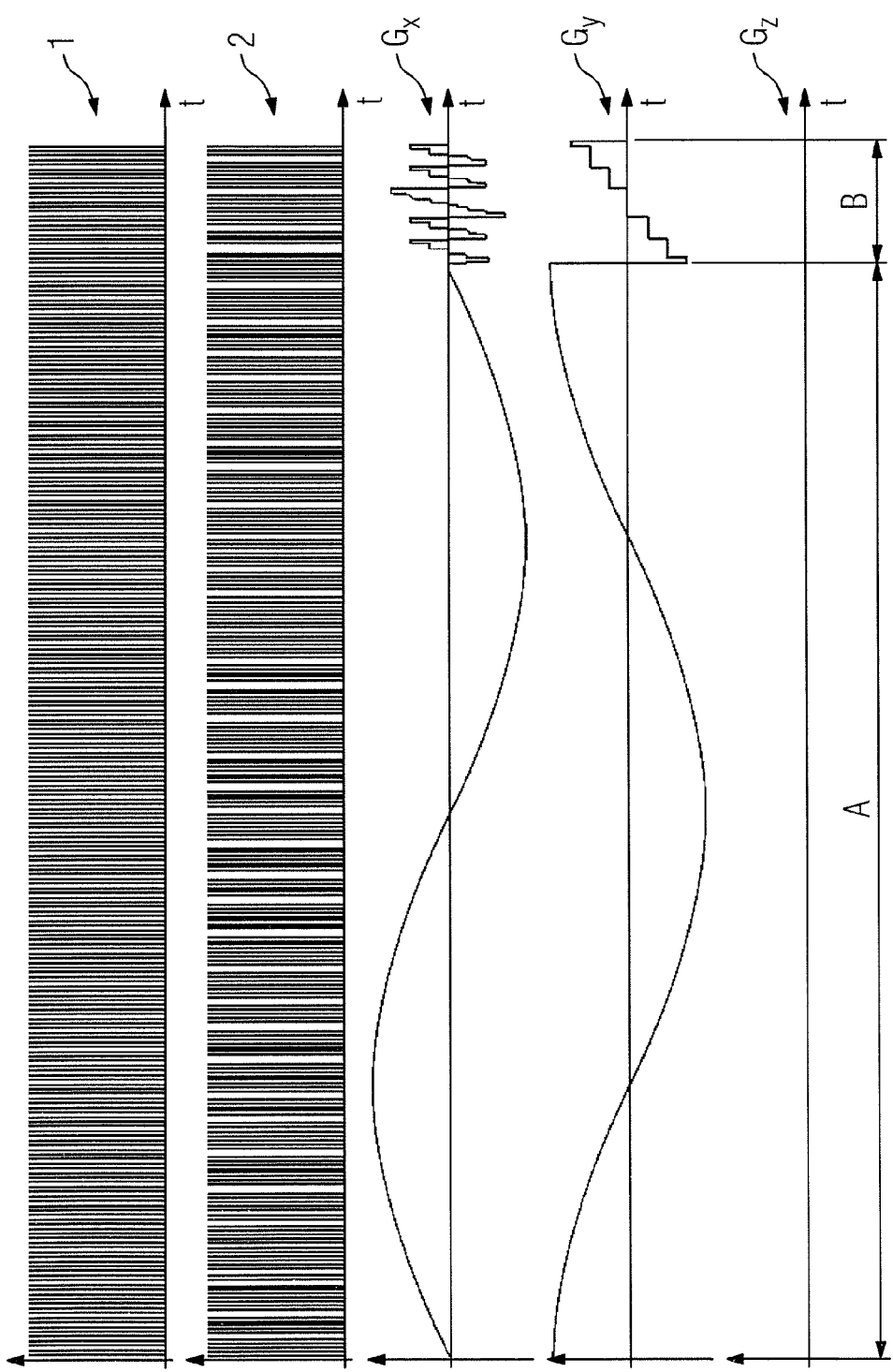
FIG. 1 shows a PETRA sequence according to the prior art for the acquisition of k-space corresponding to an imaging area.

FIG. 1 shows the workflow of a PETRA sequence as a magnetic resonance sequence as is known from the prior art (for example DE 10 2010 041 446 A1) and that can be used for image acquisition in a magnetic resonance device. The first line in FIG. 1 shows the radiated radio-frequency excitation pulses 1; the second line shows the associated readout time periods 2. The excitation pulses 1 are respectively repeated at an interval of a repetition time TR which remains constant across the entire sequence. In the present exemplary embodiment, two phase coding gradients are switched, such that a coding in the third direction (the slice direction, here the z-direction) is foregone ($G_z$=0).

Clearly, if scanning takes place both in a first measurement segment A in which a first region of k-space is scanned radially and in a second measurement segment B in which the second region of k-space (that is not included by the first region) which includes the center of k-space, the gradients are varied only very slightly (in particular continuously in the measurement segment A) so that an extremely quiet acquisition of the raw data is possible.

Figure 2:
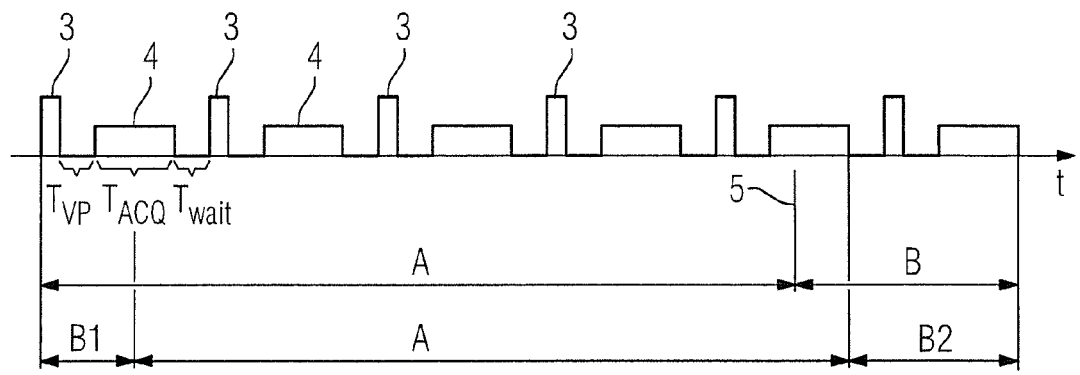
FIG. 2 is a flowchart of a measurement in which pre-pulses are radiated according to the prior art and in the method according to the invention.

In the present exemplary embodiment, a case is considered in which an inversion pulse is provided to establish a T1 contrast between white and grey brain matter as a pre-pulse for a defined number of repetitions, such that the entirety of the repetitions (measurement processes) are distributed to multiple pre-pulses as they result via combinations of excitation pulses 16 and readout times 17, as is schematically presented in FIG. 2. The pre-pulses 3 are schematically shown with the subsequent measurement time periods 4. In the following, the wait time before the measurement can begin after a pre-pulse 3, and is designated with $T_{VP}$; the measurement duration in a measurement time period 4 (which is a multiple of the repetition time TR) is designated with $T_{ACQ}$; and the optional further wait time period before the next pre-pulse 3 should be designated with $T_{wait}$. Given the regular use of the pre-pulses 3 and the respective identically long times $T_{VP}$, $T_{ACQ}$ and $T_{wait}$, a steady state results in which the magnetization curve is the same for each cycle of pre-pulse 3 and measurement time period 4.

According to the present invention, however, a deviation is made from the division into measurement segments A and B—in which the measurement of the Cartesian portion is begun at a point in time 5 (as it is shown above in FIG. 2). According to this inventive departure from conventional sequences, a portion of the measurement points situated closest to the center of k-space is measured at a particularly high contrast immediately after the first pre-pulse 3, and only then does the first measurement segment A begin for the radial scanning of k-space, followed then by the partial measurement segment B2 for the remaining measurement points of the Cartesian portion that do not correspond to the central measurement points (as shown below in FIG. 2).

Figure 3:
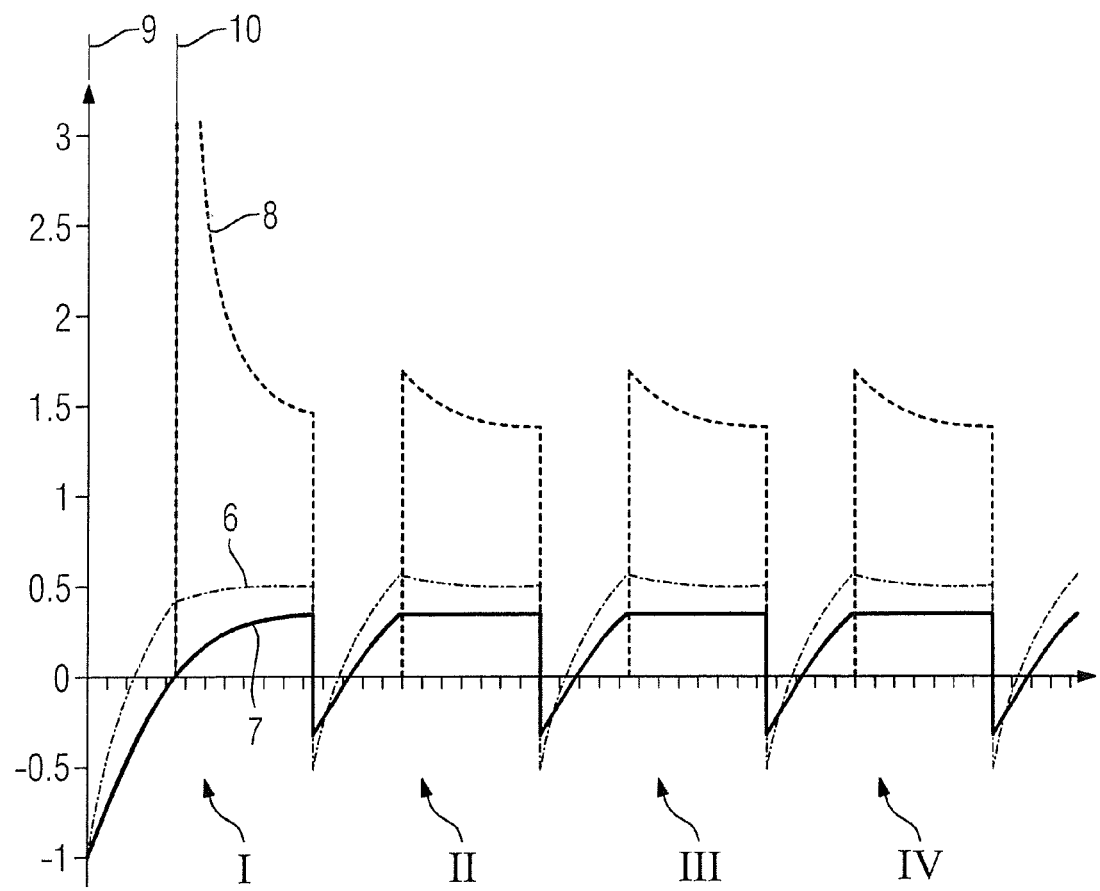
FIG. 3 shows the curve of transverse magnetizations of different materials given a pre-pulse promoting the T1 contrast for multiple cycles.

FIG. 3 shows the time curve of the transverse magnetizations for white brain matter (curve 6) and grey brain matter (curve 7). The curve 8 shows the relationship of the magnetizations to one another. The curves thereby begin immediately after a point in time 9 at which the first provided pre-pulse (here an inversion pulse) ends; the inversion of the maximum relaxed transversal magnetizations consequently occurred.

From FIG. 3 it can be seen that the steady state has already been set as of the second cycle II, which means that the magnetizations according to the curves 6, 7 always travel the same in the cycles II, III, IV, . . . However, the cycle I markedly differs after the first pre-pulse, which consequently represents the transient event leading to the steady state. Because a completely relaxed magnetization is assumed, higher values for the magnetization clearly result, wherein it is in particular noticeable that a distinctly higher value for the transverse magnetization of the white brain matter (curve 6) is already present for the transverse magnetization than in the later cycles II, III, IV. An excellent T1 contrast is consequently realized at the point in time 10, which is not repeated in this way in the later cycles. Therefore, a time period as of the point in time 10 (the partial measurement segment B1) is therefore used in order to already measure some points (for example 27 or 125 points) that lie closest to the center of k-space. The optimal conditions that arise only during the transient phase—but not in the steady state—are thus utilized.

As a start point of the measurement of these central measurement points, the point in time 10 is selected at which the transversal magnetization of the grey brain matter has its zero crossing, concretely thus at $\ln(2)*T1_{grey}$. As can be seen from FIG. 3, at this point in time the transversal magnetization of the white brain matter has already relaxed to nearly 50%, such that this delivers a high signal contribution.

It is noted that the measurements in the other cycles—thus initially the radial scanning of k-space in the first measurement segment A as presented according to FIG. 2—must not begin at the optimal point in time 10 in the first cycle I after the pre-pulse 3; rather, other settings can naturally be selected, such as for which no expressed difference is achieved between the signal of grey brain matter and white brain matter (for example $S_W/S_G=1.5$). This is possible since the k-space center (that is important for the contrast) has already been measured with optimal contrast.

The measurement of the central measurement points in the partial measurement segment B1 thereby takes place so that initially the point placed closest to the center of k-space—in particular a point placed in the center of k-space—is measured, and then a spiral-like acquisition trajectory is used that ensures that the additional central measurement points are measured in order according to their distance from the center of k-space.

Figure 4:
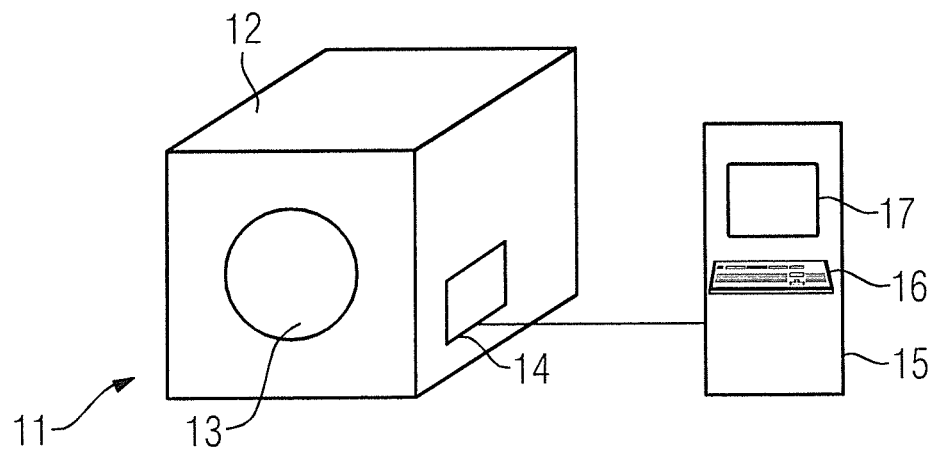
FIG. 4 schematically illustrates a magnetic resonance device according to the invention.

FIG. 4 shows a basic format of a magnetic resonance device 11 according to the invention. Such a device, this has a basic magnet unit 12 in which a patient can be moved through a patient receptacle 13. The patient receptacle 13 can surround a radio-frequency transmission/reception device, for example a body coil (not shown in detail for clarity), and the gradient coils can be provided.

The operation of the magnetic resonance device 11 is controlled by a control device 14 that cause the PETRA magnetic resonance sequence to be executed with the set sequence parameters in the image acquisition. The control device 14 is connected with an operating unit 15 which has a display device 17 and an input device 16. Adjustable sequence parameters can hereby be set—for example a number of radial spokes to be acquired—according to the desire of a user.

The control device 14 is designed to implement the method according to the invention, meaning that it adapts the acquisition activity so that the central measurement points are measured in the transient event after the administration of the first pre-pulse.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance (MR) measurement data from an examination subject, comprising:

operating an MR data acquisition unit according to an MR data acquisition sequence to acquire MR measurement data from an examination region of an examination subject in the MR data acquisition unit;

in said MR data acquisition sequence, acquiring said MR measurement data in a plurality of individual MR data acquisitions by radiating a plurality of excitation pulses;

also in said MR data acquisition sequence, radiating a pre-pulse before a predetermined number of said individual MR data acquisitions that produces a magnetization of nuclear spins of at least two materials in said imaging region, said magnetization being a source of contrast between said at least two materials in an image of the imaging region to be reconstructed from said MR measurement data;

entering said MR measurement data into an electronic memory organized as k-space corresponding to said imaging region, by entering MR measurement data into a first region of k-space, which does not include a center of k-space, radially along spokes emanating from the center of k-space, and entering MR measurement data into a second central region of k-space, which remains without said first region, in a Cartesian manner;

entering MR measurement data into at least one portion of said second region of k-space that is situated nearest the center of k-space, as central measurement points after a first radiation of said pre-pulse following a zero crossing of the magnetization of one of said at least two materials; and making k-space filled with said MR measurement data available from said memory in electronic form as a data file.

2. A method as claimed in claim 1 comprising operating said MR data acquisition unit according to a PETRA sequence, as said MR data acquisition sequence.

3. A method as claimed in claim 1 comprising entering said MR measurement data into said second region of k-space in a Cartesian manner by single point imaging.

4. A method as claimed in claim 1 comprising entering said central measurement points into said portion of said second region of k-space immediately following said zero crossing.

5. A method as claimed in claim 1 comprising radiating said pre-pulse as an inversion pulse that establishes a T1 contrast.

6. A method as claimed in claim 1 comprising beginning entry of said central measurement points into said portion of said second region of k-space after a weighting time following radiation of said pre-pulse.

7. A method as claimed in claim 1 comprising starting entry of said central measurement points into said portion of said second region of k-space with a central measurement point corresponding to the center of k-space.

8. A method as claimed in claim 1 comprising entering $n^3$ points situated closest to the center of k-space as said central measurement points, with n=2, 3, 4 or 5.

9. A method as claimed in claim 1 comprising entering said central measurement points into k-space along a spiral-like trajectory in k-space, starting from a central measurement point situated closest to the center of k-space.

10. A method as claimed in claim 1 comprising completely ramping up at least two phase coding gradients, that spatially encode said MR measurement data, before radiating the respective excitation pulses.

11. A magnetic resonance (MR) apparatus comprising:
an MR data acquisition unit;
a control unit configured to operate the MR data acquisition unit according to an MR data acquisition sequence to acquire MR measurement data from an examination region of an examination subject in the MR data acquisition unit;
said control unit, in said MR data acquisition sequence, being configured to operate the MR data acquisition unit to acquire said MR measurement data in a plurality of individual MR data acquisitions by radiating a plurality of excitation pulses;
said control unit, also in said MR data acquisition sequence, being configured to operate the MR data acquisition unit to radiate a pre-pulse before a predetermined number of said individual MR data acquisitions that produces a magnetization of nuclear spins of at least two materials in said imaging region, said magnetization being a source of contrast between said at least two materials in an image of the imaging region to be reconstructed from said MR measurement data;
said control unit being configured to enter said MR measurement data into an electronic memory organized as k-space corresponding to said imaging region, by entering MR measurement data into a first region of k-space, which does not include a center of k-space, radially along spokes emanating from the center of k-space, and entering MR measurement data into a second central region of k-space, which remains without said first region, in a Cartesian manner;
said control unit being configured to enter MR measurement data into at least one portion of said second region of k-space that is situated nearest the center of k-space, as central measurement points after a first radiation of said pre-pulse following a zero crossing of the magnetization of one of said at least two materials; and
said control unit being configured to make k-space filled with said MR measurement data available in electronic form as a data file.

* * * * *